(12) United States Patent
Stanford et al.

(10) Patent No.: US 6,596,282 B1
(45) Date of Patent: Jul. 22, 2003

(54) **TREATMENT OF CHRONIC VIRAL INFECTIONS WITH *M. VACCAE***

(75) Inventors: John L. Stanford, Kent (GB); Graham A. W. Rook, London (GB); Cynthia A. Stanford, Kent (GB)

(73) Assignee: Stanford Rook Limited, London (GB)

( * ) Notice: Subject to any disclaimer, the term of this patent is extended or adjusted under 35 U.S.C. 154(b) by 0 days.

(21) Appl. No.: 09/913,523

(22) PCT Filed: Feb. 16, 2000

(86) PCT No.: PCT/GB00/00544

§ 371 (c)(1),
(2), (4) Date: Sep. 13, 2001

(87) PCT Pub. No.: WO00/48615

PCT Pub. Date: Aug. 24, 2000

(30) Foreign Application Priority Data

Feb. 16, 1999 (GB) .............................................. 9903539

(51) Int. Cl.[7] .................. A61K 39/04; A61K 39/02; A61K 39/245; A61K 39/12; A61K 49/00

(52) U.S. Cl. ..................... 424/248.1; 424/9.1; 424/9.2; 424/184.1; 424/204.1; 424/225.1; 424/229.1; 424/234.1

(58) Field of Search ..................... 424/9.1, 9.2, 184.1, 424/204.1, 225.1, 229.1, 234.1, 248.1

(56) References Cited

FOREIGN PATENT DOCUMENTS

| WO | WO91/01751 | 2/1991 |
|----|------------|--------|
| WO | WO91/02542 | 3/1991 |
| WO | WO92/08488 | 5/1992 |
| WO | WO94/06466 | 3/1994 |
| WO | WO99/32634 | 7/1999 |

*Primary Examiner*—Rodney P Swartz
(74) *Attorney, Agent, or Firm*—Nixon & Vanderhye, P.C.

(57) ABSTRACT

The present invention provides the use of an *M. vaccae* preparation for the manufacture of a medicament for use in the treatment of a chronic viral infection, excluding an HIV infection. Chronic viral infections include HPV infection, such as HPV infection associated with cervical dysplasia, herpes virus infection, subacute sclerosing pan-encephalitis and hepatitis virus infection.

4 Claims, No Drawings

TREATMENT OF CHRONIC VIRAL INFECTIONS WITH *M. VACCAE*

FIELD OF THE INVENTION

The present invention relates to the use of *M. vaccae* in the treatment of viral infections, particularly chronic viral infections.

BACKGROUND TO THE INVENTION

British Specification No. 2156673 (International Patent Specification WO85/03639) describes immunotherapeutic agents comprising killed cells of *M. vaccae*. These agents are useful in the immunotherapy of mycobacterial disease, especially tuberculosis and leprosy. It is stated that use of this immunotherapeutic agent facilitates the removal of the persisting bacilli responsible for tuberculosis or leprosy which, as is well known, it is difficult to remove by chemotherapy alone.

International Patent Specification PCT/GB85/00183 (WO85/05034) describes compositions for the alleviation of the symptoms of, and for the treatment or diagnosis of, arthritic disease which comprise as active ingredient the whole organism of *M. vaccae*. It is stated that the preparations of *M. vaccae* are useful for the treatment of various autoimmune diseases and especially arthritic conditions including rheumatoid arthritis, ankylosing spondylitis or Reiter's syndrome.

Other uses of *M. vaccae* are described in, inter alia, WO91/02542, which refers to compositions comprising antigenic and immunoregulatory material derived from *M. vaccae* as being generally useful in the treatment of pathological conditions in which the proportion of agalactosyl IgG (i.e. IgG which lacks terminal galactose from the N-linked oligosaccharides on the heavy chains) is increased, WO92/08484, which refers to the use of *M. vaccae* for the treatment of uveitis, WO94/06466, which provides the use of antigenic and/or immunoregulatory materials derived from *M. vaccae* for the manufacture of a medicament useful in the therapy of AIDS and also in the therapy of HIV-positive asymptomatic patients, and South African patent application 95/2644, which teaches that immunotherapy with *M. vaccae* is expected to be effective against tumours of mesodemal, endodermal and ectodermal origin, including breast and bronchial tumours.

The therapeutic agent conveniently, and therefore preferably, comprises dead cells of *M. vaccae*, most preferably cells which have been killed by autoclaving, although WO92/08488 further discloses that killed cells of *M. vaccae* can be used to stimulate and/or modify in a favourable way the immune response to antigens which are not endogenous to *M. vaccae*.

International application PCT/GB98/03346 teaches that cold-shocked *M. vaccae* preparations may be obtained which comprise proteins induced by cold-shock treatment and that such preparations have a variety of uses, including but not limited to the treatment of diseases such as Raynaud's syndrome or hypothermia.

DISCLOSURE OF THE INVENTION

We have surprisingly found that treatment of chronic viral infections with *M. vaccae* is beneficial to the course of the infection, in either stabilizing the infection or providing partial or complete clinical improvements.

The action of *M. vaccae* against viral diseases in humans or other animals is surprising in that the action of this bacterial antigen induces a response to cells infected at a distant site by a virus.

The present invention thus provides a method of treating a chronic viral infection, excluding an HIV infection, which method comprises administering to a human or animal subject in need of treatment an effective amount of an *M. vaccae* preparation. The action against these non-HIV chronic viruses may be distinguished over the action against HIV in that HIV directly attacks the host immune system which is believed to be modulated by the action of *M. vaccae*.

The invention further provides the use of an *M. vaccae* preparation for the manufacture of a medicament for use in the treatment of a chronic viral infection, excluding an HIV infection.

DETAILED DESCRIPTION OF THE INVENTION

Certain viruses can enter specific cells, change the function of the cells to produce viral proteins and express stress proteins, without killing them. Such viruses slowly replicate within the infected host cells and such infection may cause chronic or relapsing disease, and may also produce clinical lesions. Thus by "chronic viral infection", is meant a viral infection of humans or other animals which is able to infect a host and reproduce within the cells of a host over a prolonged period of time—usually weeks, months or years, without proving fatal.

Amongst viruses giving rise to chronic infections and which may be treated in accordance with the present invention are the human papilloma viruses (HPV), Herpes simplex and other herpes viruses, the viruses of hepatitis B and C as well as other hepatitis viruses, and the measles virus, all of which can produce important clinical diseases. Prolonged infection may ultimately lead to the induction of disease which may be, e.g. in the case of hepatitis C virus liver cancer, fatal to the patient.

Papilloma viruses in man give rise to four different presentations of warts. Sporadic warts, usually on the hands, plantar warts of the foot, multiple warts in which scattered large areas of skin are involved in confluent warty excrescences, often involving the pudenda (venereal warts) and papilloma virus associated dysplasia of the uterine cervix, quite often without other lesions. The first two of these are usually minor, self-resolving or easily treated by topical measures. The second two are much more difficult to treat and usually persist lifelong to varying degrees. Cervical dysplasia is a well known premalignant condition and is the major reason for the cervical smear programme. There are at least 75 types of HPV that can be distinguished. Solitary lesions are usually associated with a single type, multiple lesions are often found to be due to several different types of virus at the same time, venereal warts and cervical dysplasia are often associated with types 16, 18 or 31 virus. These types, as well as other HPV subtypes, e.g. HPV2*a* and HPV21 may be treated in accordance with the present invention.

The herpes simplex virus HSV-1 causes the common condition known as "cold sores" in which small raised or ulcerated lesions occur several times a year, at the mucocutaneous junction between the buccal or nasal mucosa and the surrounding skin. Frequently the lesions occur when immunity is impaired by acute virus infections. The viruses survive longterm in small nerve endings. The HSV-2 virus can also give rise to genital herpes in which extensive lesions occur around the mucocutaneous junction between the glans penis and prepuce or around the vulva. In both sexes genital herpetic lesions tend to be much more extensive and severe than are cold sores. Fluctuating from time to time, genital herpes is much more persistent than are cold sores. Again, the virus becomes established in small nerves from which it continuously reinfects the pudendal regions. The present invention provides for treatment of both HSV-1 and HSV-2 infection, as well as for the treatment of other herpes viruses.

Hepatitis B and C viruses are usually, though perhaps not solely, transmitted from person to person with blood products. Both give rise to an acute hepatitis that in some people resolves without further problems and in others becomes chronic. Chronic hepatitis results in slow cirrhosis is of the liver that may lead to death due to liver failure or to development of malignant hepatomas. Neither disease is at all easily treated.

Very rarely the measles virus can become established chronically in the brain and give rise to a progressive and fatal condition called subacute sclerosing pan-encephalitis (SSPE), for which there is no known treatment.

Other chronic viral infections which may be treated in accordance with the present invention include Epstein Barr virus (EBV), as well as other viruses such as those which may be associated with tumours, or in the case of animals, various veterinary viral diseases, for example those of domestic pets or farmyard animals important in agriculture.

It will be understood that the action of treatment of the infection is moderate, alleviate or remove the symptoms of the infection, or delay or prevent the onset of secondary changes such as malignancies or other morphological changes, by reducing the severity of infection by removal or reduction of the viral load or otherwise.

The *Mycobacterium vaccae* preparation may be material which can be or include dead cells of *M. vaccae*. Such cells may be killed, for instance using irradiation, e.g. from $^{60}$Cobalt at a dose of 2.5 megarads, chemically, or by any other means, although autoclaving is preferred, e.g. at 69kPa for 10 minutes at 115° C.–125° C. Autoclaving may yield a more effective preparation than irradiation.

Prior to being killed, *M. vaccae* cells may be grown on a suitable solid medium. A modified Sauton's liquid medium may be preferred (Boyden et al.), solidified with agar, preferably 1.3% agar. After aerobic incubation, generally at 32° C. for 10 days, the organisms may be harvested, then weighed and suspended in diluent, ready for administration. Storage, if required before use, may be at 4° C.

Instead of growing the cells on a solid medium, a liquid medium, such as the modified Sauton's medium (Boyden et al.), may be employed, for instance in a fermentor.

During growth, the *M. vaccae* may be treated by a cold-shock or a heat-shock in order to induce the production of cold- or heat-shocked proteins. Suitable heat-shock conditions include a period of growth at an elevated temperature, e.g. 37, 42 or 45° C. for a period of time from 10 minutes to several, e.g 3 or more hours. Cold-shock treatment may be performed for similar periods of time at reduced temperatures, e.g. from 10 to 25° C.

The diluent may be unbuffered saline, pyrogen-free. Preferably, the diluent is borate-buffered, preferably containing a surfactant such as Tween 80®. A suitable borate buffer is: $Na_2B_4O_7.10H_2O$—3.63 g, $H_3BO_3$—5.25 g, NaCl—6.19 g, Tween 80® 0.0005%, distilled water to 1 litre. These diluents are pharmaceutically acceptable.

The human results mentioned above have been obtained by administration of *M. vaccae* as the GMP preparation, SRL172, which is available for human use under several investigator IND's from the Federal Drug Administration, and CTX's from the Medicines Control Agency in the UK. GLP acute toxicology has been performed by Huntingdon Research. Phase 1 and Phase 2 safety data have been obtained in the USA, and lodged with the FDA. SRL172 is in Phase 3 trials for the immunotherapy of tuberculosis. SRL172 may be preferred for use in the present invention.

SRL172 is a *M. vaccae* formulation derived from the strain denoted R877R which was deposited under the Budapest Convention at the National Collection of Type Cultures (NCTC) Central Public Health Laboratory, Colindale Avenue, London NW9 5HT, United Kingdom, on Feb. 13, 1984 under the number NCTC 11659. R877R was originally isolated from mud samples from the Lango district of Central Uganda (Stanford and Paul).

Other *M. vaccae* strains may be used instead of SRL172. An organism can be identified as belonging to *M. vaccae* by biochemical and antigenic criteria (Bonicke et al.).

It is preferred for the present invention that the *M. vaccae* material is administered free or substantially free from non-*M. vaccae* antigenic or immunoregulatory material. In other words the medicament or composition to be administered may include, or may consist essentially of, *M. vaccae* antigenic and/or immunoregulatory material, such as dead cells, an extract or derivative thereof, and a pharmaceutically acceptable diluent.

Administration is preferably in a "therapeutically effective amount", this being sufficient to show benefit to a patient. Such benefit may be at least amelioration of at least one symptom. The actual amount administered, and rate and time-course of administration, will depend on the nature and severity of what is being treated. Prescription of treatment, eg decisions on dosage etc, is within the responsibility of general practioners and other medical doctors.

A single dosage (where dead cells are to be administered) will generally contain from $10^7$ to $10^{10}$ killed *M. vaccae* microorganisms. Patients may be administered a single dose of $10^8$ to $10^9$ killed *M. vaccae*, though the dose may be repeated if need be, for instance at intervals from 2 weeks to 6 months.

A composition may be administered alone or in combination with other treatments, either simultaneously or sequentially dependent upon the condition to be treated.

Pharmaceutical compositions according to the present invention, and for use in accordance with the present invention, may include, in addition to active ingredient, a pharmaceutically acceptable excipient, carrier, buffer, stabiliser or other materials well known to those skilled in the art. Such materials should be non-toxic and should not interfere with the efficacy of the active ingredient. The precise nature of the carrier or other material will depend on the route of administration, which may be by any convenient route for those of skill in the art, though is preferably by injection, e.g. cutaneous, subcutaneous or intra-dermal.

For injection, the active ingredient will be in the form of a parenterally acceptable aqueous solution which is pyrogen-free and has suitable pH, isotonicity and stability. Suitable diluents, which are pharmaceutically acceptable and may be preferred, have been discussed already above.

Oral administration may be used, in which case the pharmaceutical composition may be in tablet, capsule, powder or liquid form. A tablet may include a solid carrier such as gelatin or an adjuvant. Liquid pharmaceutical compositions generally include a liquid carrier such as water, petroleum, animal or vegetable oils, mineral oil or synthetic oil. Physiological saline solution, dextrose or other saccharide solution or glycols such as ethylene glycol, propylene glycol or polyethylene glycol may be included.

*M. vaccae* may be administered by aerosol to the airways, using a suitable formulation, e.g. including particles of a size which travels to the appropriate parts of the airways. This may be a dried powder rather than aqueous suspension.

Instead of killed cells, material derived from *M. vaccae* may be used, in particular an extract or a synthetic molecule which has the requisite activity.

The invention is illustrated by the following non-limiting examples, which report case studies of patients receiving one or more standard doses ($10^8$–$10^9$ cells) of *M. vaccae*.

EXAMPLE 1

Two individuals receiving immunotherapy with killed *M. vaccae* for other indications had longstanding solitary warts on their hands, presumed to be of viral origin. During treatment, complete disappearance of the warts was observed.

EXAMPLE 2

Three patients with extensive multiple warts caused by a variety of HPV subtypes have received series of injections of killed *M. vaccae*.

The first of these was a 15 year old boy with an immune defect following bone marrow reconstitution from a parental source for severe combined immunodeficiency, aged 5 months. He is infected with HPV2a and 21, and had developed severe intractable warts 8 years ago. Over the past year he has received 7 injections of *M. vaccae*, following some of which increases in IL-2 production and CD8 cytotoxic-cells occurred. However, these were not maintained. Progress of the clinical lesions is ongoing and being monitored for improvements.

The second case was of a woman aged 29 years who first developed a finger wart aged 9, had large-scale involvement of her hands and feet by the age of 15 and developed genital warts by the time she was 19. Cervical cytology, first carried out when she was 20 years old, has continued to show borderline to moderate dyskaryosis ever since, for which she has received several local diathermy and cold coagulation treatments. She has received two courses of 3 doses of *M. vaccae*, the first at monthly intervals between March and May 1998, and the second more recently at 2-week intervals. She is currently being followed-up for signs of clinical benefit.

The third case is a woman aged 54, who has received three monthly doses of *M. vaccae*, and is now being monitored for response.

EXAMPLE 3

A woman of 38 years had a history of 6-monthly cervical smears showing dysplasia for the past 20 years, during which time she had borne 3 children and received local laser therapy. Following a single injection of killed *M. vaccae* in 1995 her next 2 regular cervical examinations were normal for the first time in the 22 years. Subsequently she has received 4 further annual injections of killed *M. vaccae* and cervical examinations, the last one being on May 19, 1999. Since commencing treatment all smear tests have been clear.

EXAMPLE 4

A woman of 34 years, with a history of development of genital herpes 3 months previously, received two-monthly injections of killed *M. vaccae* and a third three months later. The patient was examined 15 months after the first injection and reported that she had been, and remained, free of symptoms since receiving the treatment. Over this period she was expected to have suffered from 2 or 3 recurrent episodes of the disease, despite continuous treatment with antiviral chemotherapy.

EXAMPLE 5

A 9 year old girl with a history of congenital toxoplasmosis presented a year ago with progressive SSPE following vaccination against measles. With the lack of any alternative treatment, a trial of immunotherapy with killed *M. vaccae* was started in October 1997. Over the first 15 months of treatment she received repeated injections of *M. vaccae* and her disease progressed little, if at all, i.e. there was no significant deterioration in her condition. Over the following 12 months she received twice weekly injections and considerable improvements were observed. The patient regained the ability to sit by herself. Large movements with eyes, head, neck arms, and legs were reported, and she was observed to play purposively. Analysis of the cerebrospinal fluid antibodies revealed a change from polyclonal antibodies against measles virus (associated with progressive disease) to oligoclonal (associated with recovery from virus infection).

All publications and patent applications cited in this specification are herein incorporated by reference as if each individual publication or patent application were specifically and individually indicated to be incorporated by reference.

Although the foregoing invention has been described in some detail by way of illustration and example for the purposes of clarity and understanding, it will be readily apparent to those of skill in the art that certain changes and modifications may be made thereto without departing from the spirit or scope of the appended claims.

References

Bonicke et al., (1964) Zentr albl. Bakteriol. Parasitenkd. Infection skr. Hyg. Abt. 1, Orig., 192: 133 Boyden et al., (1955) J. Inmunol. 75: 15. Stanford and Paul, (1973) Ann. Soc. Belge Med. Trop. 53: 141–389.

What is claimed is:

1. A method of treating a chronic viral infection, excluding an HIV infection, which method comprises administering to a human or animal subject in need of treatment an effective amount of a preparation comprising dead cells of *M. vaccae* wherein said chronic viral infection is selected from the group consisting of HPV infection, a herpes virus infection and subacute sclerosing pan-encephalitis.

2. A method according to claim 1 wherein said subject has cervical dysplasia as a result of HPV infection.

3. A method according to claim 1 wherein said herpes virus infection is a herpes simplex virus infection.

4. A method of treating a chronic viral infection, excluding an HIV infection, which method comprises administering to a human or animal subject in need of treatment an effective amount of a preparation comprising dead cells of *M. vaccae*, said preparation being substantially free of non *M. vaccae* antigenic material and wherein said chronic viral infection is selected from the group consisting of HPV infection, a herpes virus infection and subacute sclerosing pan-encephalitis.

* * * * *